(12) United States Patent
Dalmia et al.

(10) Patent No.: US 6,908,538 B2
(45) Date of Patent: Jun. 21, 2005

(54) ELECTROCHEMICAL GAS SENSOR HAVING A POROUS ELECTROLYTE

(75) Inventors: Avinash Dalmia, Hamden, CT (US); Otto J. Prohaska, Beacon Fall, CT (US)

(73) Assignee: PerkinElmer Instruments LLC, Shelton, CT (US)

( * ) Notice: Subject to any disclaimer, the term of this patent is extended or adjusted under 35 U.S.C. 154(b) by 349 days.

(21) Appl. No.: 10/053,458

(22) Filed: Oct. 22, 2001

(65) Prior Publication Data

US 2003/0075438 A1 Apr. 24, 2003

(51) Int. Cl.⁷ ............................................. G01N 27/403
(52) U.S. Cl. ..................................... 204/431; 204/432
(58) Field of Search ................................. 204/415, 424, 204/431, 432

(56) References Cited

U.S. PATENT DOCUMENTS

| | | | |
|---|---|---|---|
| 4,668,374 A | 5/1987 | Bhagat et al. | |
| 5,281,324 A | * 1/1994 | Kiesele et al. | 204/415 |
| 5,304,293 A | 4/1994 | Tierney et al. | |
| 5,421,984 A | * 6/1995 | Saito et al. | 204/426 |
| 5,821,402 A | 10/1998 | Okajima et al. | |
| 5,866,204 A | 2/1999 | Robbie et al. | |
| 6,012,327 A | 1/2000 | Seth et al. | |
| 6,041,643 A | 3/2000 | Stokes et al. | |
| 6,129,824 A | * 10/2000 | Rollick et al. | 204/412 |

* cited by examiner

*Primary Examiner*—Kaj K. Olsen
(74) *Attorney, Agent, or Firm*—St. Onge Steward Johnston & Reens LLC

(57) ABSTRACT

The invention relates to an electrochemical gas sensor having improved response time and sensitivity. The electrochemical gas sensor includes a substrate for providing a surface upon which an electrode may be placed, a first electrode placed on the surface, a thin film of electrolyte support for receiving electrolyte and having a predetermined porosity, and a second electrode deposited on the thin film for permitting a measurement of current between the first and second electrodes.

12 Claims, 4 Drawing Sheets

ELECTROCHEMICAL GAS SENSOR HAVING A POROUS ELECTROLYTE

FIELD OF INVENTION

The invention relates to an electrochemical gas sensor having improved sensitivity and response time and, more particularly, a sensor having a thin, rigid layer having a predetermined porosity for receiving an electrolyte.

BACKGROUND OF THE INVENTION

Monitoring toxic gases is a great concern in relation to environmental pollution, occupational health, and industrial emission control. Known methods and apparatuses have been developed to detect the presence of gas. For example, gas chromatography, ion chromatography, electrolytic conductivity detection, and conductometric measurement are typically used to detect gas. However, these manners for detecting gas have generally been expensive, cumbersome, shown to have poor sensitivity and slow response times. They also typically cannot readily be used for on-line measurements. Other manners for monitoring include capacitance sensors and surface acoustic wave sensors. However, the sensitivities, or detection capabilities, of these devices generally fall in the range of low-ppm to high-ppb.

Electrochemical sensors were provided to overcome these limitations. Electrochemical sensors typically operate at room temperature, provide a signal which varies with concentrations of analyte species, have short response time, and exhibit acceptable sensitivity, stability, and reproducibility. In addition, electrochemical sensors are compact and can be used for continuous monitoring. Known electrochemical sensors include both liquid and solid electrolytic layers.

Other known electrochemical gas sensors typically include metal layers or gas diffusion electrodes in contact with an electrolytic film of, for example, Nafion or Teflon. The cornerstone of these sensors generally has been on optimizing the metal/gas/ionic medium interface in order to achieve higher sensitivity. However, the assembly processes for these sensors are manually intensive and are not suited for automated mass production.

Recently, planar thin film sensors have been developed by constructing three planar electrodes on an insulating substrate and covering them with a thin polymer electrolyte, such as Nafion. J. A. Cox and K. S. Alber, *Amperometric Gas Phase Sensor for the Determination of Ammonia in a Solid State Cell Prepared by a Sol-Gel Process*, 143, No. 7 J. Electrochem. Soc. L126–L128 (1996) developed a solid state cell in which microelectrode arrays were coated with a film of vanadium oxide xerogel for detection of ammonia. However, this film needs to be soaked in an electrolyte solution in order to provide ionic conductivity. These methodologies, in which a planar substrate with metal electrodes is covered with a thin film of solid state electrolytic material, are suitable for automated mass production, but they have lower sensitivity since gas needs to diffuse through a relatively thick film of electrolyte.

U.S. Pat. No. 5,866,204 to Robbie et al. ("'204 patent") discloses a method of making a vapor deposited thin film by introducing vapor at varying angles onto a substrate. The '204 patent claims a film forming method that allows for the growth of complex microstructures with predetermined patterns of growth and porosity. However, the '204 patent does not disclose use of the vapor deposited thin film for detecting gas or in conjunction with an electrochemical sensor. Furthermore, no reference discloses depositing metal, for use as an electrode, on top of an electrolytic film.

What is desired, therefore, is to provide an electrochemical sensor suitable for mass production and having improved sensitivity. What is further desired is to provide an electrochemical sensor having detection capabilities desirably in the range of sub-ppb to low ppb levels. What is yet further desired is to provide an electrochemical sensor having improved response time.

SUMMARY OF THE INVENTION

Accordingly, it is an object of the invention to provide an electrochemical gas sensor including a thin layer of a material having a predetermined porosity for use as an electrolyte support.

It is also an object of the invention to provide an electrochemical gas sensor including a thin layer of a material having a plurality of columns for use as an electrolyte support.

It is yet another object of the invention to provide an electrochemical gas sensor having an electrolyte solution placed between the plurality of columns.

It is still an object of the invention to provide an electrochemical gas sensor, whereby the plurality of columns further includes a cap for depositing an electrode thereon.

It is still another object of the invention to provide an electrochemical gas sensor having a thin metal film deposited on top of an electrolyte support.

It is still a further object of the invention to provide an electrochemical gas sensor, whereby a sensing electrode further includes a coating for preventing flooding by electrolyte solution.

It is yet another object of the invention to provide an electrochemical gas sensor having a metal layer that improves lamination to the electrolytic layer.

It is still a further object of the invention to provide a method for making an electrochemical gas sensor including forming a plurality of columns and capping the electrolyte support.

It is yet another object of the invention to provide a method for making an electrochemical gas sensor including forming a thin film for electrolyte support by directing vapor towards the substrate in a generally angular direction for forming the plurality of columns and rotating the substrate about an axis generally parallel to a plane of the substrate for capping the thin film.

These and other objects of the invention are achieved by an electrochemical gas sensor having improved response time and sensitivity. The electrochemical gas sensor includes a substrate for providing a surface upon which an electrode may be placed, a first electrode placed on the surface, a thin film of electrolyte support for receiving electrolyte and having a predetermined porosity, and a second electrode deposited on the thin film for permitting a measurement of current between the first and second electrodes.

Electrochemical gas sensor may further include a thin film of electrolyte support having a plurality of columns for holding electrolyte, thereby minimizing the overall thickness of the electrolytic layer to be that of a thin film. The plurality of columns may have a variety of geometric shapes, such as being helix shaped, and may be made of an insulating and insoluble material capable of absorbing solution.

The electrochemical gas sensor may further include a hydrophobic coating on the second electrode for preventing flooding by the liquid electrolyte.

The electrochemical gas sensor may also have an electrolytic layer that further includes a cap upon which the second electrode may be deposited.

The porosity of the plurality of columns is ideally large so as to maximize electrolyte absorption. Porosity is between 5% and 50% and, preferably, 5% and 80% and pore size in the range of between 0.0002 and 2 micrometers and, preferably, 0.0002 and 10 micrometers. Furthermore, the sensing electrode has a porosity less than the porosity of the electrolyte support and, preferably, has a porosity magnitudes less. The sensing electrode should have a porosity of less than 5% and a pore size not exceeding the smaller of either a width or length of the sensing electrode at the pore's greatest measurement. Deposition of the sensing electrode has an additional advantage of providing improved lamination-to the electrolyte support.

In another aspect of the invention, the invention may include a method for providing an electrolyte support layer, including depositing a thin film of electrolyte support on a substrate and first electrode by forming a plurality of columns to hold electrolyte solution, capping the thin film of electrolyte support, and depositing a second electrode on the capped film.

The method may further include saturating the electrolyte support in order to form an electrolytic film. The method may also include coating the second electrode for preventing flooding by electrolyte solution.

Capping the electrolyte support includes rotating the substrate at varying degrees to the source of deposition. After capping, metal, such as an electrode, may be deposited on the capped electrolyte support to provide improved lamination to the electrolyte support.

In another aspect of the invention, the electrochemical gas sensor may include a method for providing an electrolyte support layer, including directing vapor towards the substrate in a generally angular direction for forming a plurality of columns and rotating the substrate about an axis generally parallel to a plane of the substrate for capping the thin film.

The method may further include forming helically shaped columns by rotating the substrate about an axis generally perpendicular to the plane of the substrate.

The invention and its particular features and advantages will become more apparent from the following detailed description considered with reference to the accompanying drawings.

DETAILED DESCRIPTION OF THE DRAWINGS

Figure 1:
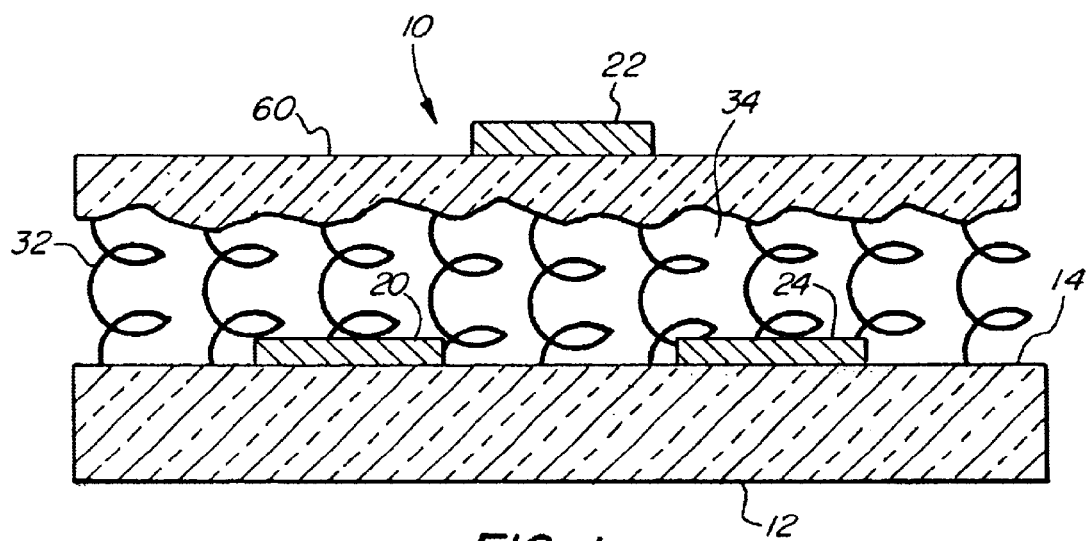
FIG. 1 depicts the electrochemical gas sensor in accordance with the invention.

FIG. 1 depicts electrochemical gas sensor 10 in accordance with the invention. Electrochemical gas sensor 10 comprises substrate 12, surface 14 of substrate 12, first electrode 20, second electrode 22, and electrolyte having a predetermined porosity. Electrochemical gas sensor 10 may further include third electrode 24.

Electrochemical gas sensor 10 operates to detect the presence of a desired gas in an unknown mixture of gases. A measurement of current is taken between first and second electrodes, 20 and 22. The electrolytic layer is in contact with both first and second electrodes and acts as a conductive medium to carry current or ions between first and second electrodes, 20 and 22. It should be known that current may also flow from second to first electrodes, 22 and 20, and that first and second electrodes are interchangeable.

When an unknown gas mixture comes into contact with electrochemical gas sensor 10, it undergoes oxidation or reduction yielding an increased current flow between first and second electrodes, 20 and 22. In the case of $SO_2$, the reaction for detecting the species of interest is as follows:

At the sensing electrode:  $SO_2 + 2H_2O \rightarrow SO_4^{2-} + 4H^+ + 2e^-$ At the counter electrode: 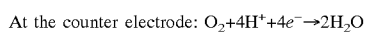 $O_2 + 4H^+ + 4e^- \rightarrow 2H_2O$ Substrate 12 includes known or novel materials used for forming the housing of electrochemical gas sensor 10 and the supporting surface 14 upon which first electrode 20 is deposited. The substrate has a surface that is generally, although not necessarily, flat so that a desirably thin film of conductive material may be deposited thereon free from unnecessary pores or crevices.

Suitable materials include glass or any nonconductive material so as not to electrically short-circuit the electrodes.

First electrode 20 is deposited on surface 14 for providing an electrical connection with second electrode 22 via the electrolytic layer. First electrode 20 is depicted in FIG. 1 as the counter electrode and second electrode 22 is depicted as the sensing or working electrode. As stated above, first and second electrodes, 20 and 22, are interchangeable and second electrode 22 may be the counter electrode whereas first electrode 20 may be the sensing electrode. Further, current may flow in either direction, whether to or from first or second electrode.

First electrode 20 and second electrode 22 include any known or novel conductive material suitable for conducting electricity. Generally, a metallic material, such as platinum, is used but any material permitting electrical current to flow suffices.

First electrode 20 is applied using known or novel methods for applying thin films, including spin/sputter coating or evaporating the electrodes onto surface 14. In addition, electrochemical gas sensor 10 may further include third electrode 24 deposited on surface 14. Third electrode 24 is not necessary for proper functioning of electrochemical gas sensor 10 but provides a more desirable sensor for stability and/or repeatability are improved. If first electrode 20 operates as a counter electrode, third electrode 24 may function as a reference electrode which provides a stable and controlled potential at the working electrode, independent of the voltage at the counter electrode. Similar to the first and second electrodes, third electrode 24 may be interchanged with either of first and/or second electrode, 20 and/or 22, and includes all the limitations described herein for the first and second electrodes. However, for the purposes of FIG. 1, third electrode 24 is depicted as the reference electrode.

Like first electrode 20, second and third electrodes, 22 and 24, are also coated onto surface 14 and the electrolytic support layer using novel or conventional thin and thick film deposition techniques, including spin/sputter coating or evaporation. Photolithographic structuring techniques permit the electrodes to be placed in desirable locations within electrochemical gas sensor 10. As depicted in FIG. 1, it is desirable, but not necessary, for the first and third electrodes to be photolithographically spaced apart from each other on surface 14. It is also desirable to coat second electrode 24 on the electrolytic support layer but horizontally between the first and second electrodes.

Second electrode 22 is desirably a thin film so as to reduce wicking and porosity, both of which are undesirable. Second electrode 22 has a porosity lower than the porosity of the thin film of electrolyte support. Generally, second electrode 22 has a porosity 10 times less, preferably much less, or orders of magnitude less porous than the thin film of electrolyte support. In certain embodiments, second electrode 22 has a porosity of less than 5% and a pore size not exceeding the smaller of either a width or length of second electrode 22 at a pore's greatest measurement. A porous surface causes bubbles to form on the electrode surface and this interferes with the electrical reaction for bubbles prevent electrolyte from contacting the electrode, which is necessary for the electrical reaction. Wicking is penetration of electrolyte into the electrode surface and causes the same undesirable bubble formation. A thin film is desired, but not required, for sensor 10 to function properly for a thin film lacks the requisite thickness to permit a pore to completely form, thereby preventing wicking or undesirable bubble formation. Without wicking or undesirable bubble formation, sensor 10 provides a more accurate result and quicker response time. Further, first and third electrodes may also be a thin film but their role as far as wicking is concerned, although secondary, is not as critical to sensor response time and accuracy as second electrode 22.

In addition, when deposited on the electrolyte support, second electrode 22, the sensing electrode, provides improved lamination to the electrolyte support. Improved lamination resists rupture, cracking, or peeling of the electrolyte support or separation of plurality of columns 32 from one another. A deposited metal film, or second electrode 22, hinders delamination because the metal film acts as a cover that binds localized areas of the electrolyte support.

The electrolytic support layer includes a thin film of an electrically conductive medium 34 for carrying a flow of ions or current between first and second electrodes, 20 and 22. The conductive medium 34 also carries a flow of ions or current between third electrode 24, if applicable, and either first or second electrode. The electrolytic support layer further includes a plurality of columns 32 formed by a glancing angle deposition ("GLAD") process. The electrolytic support layer formed using the GLAD process produces a film having a predetermined porosity and pore size. Further, electrolytic support layer, being porous and having spaces in between the plurality of columns, acts as a mechanism for holding a conductive medium 34, such as an electrolyte. Electrolytic support layer formed using the GLAD process has a porosity in the range of 5%–50% and a pore size in the range of 0.01–1 microns. Because increased porosity and pore size is desirable for holding electrolyte 34, the electrolytic support layer may have porosity in the range of 5%–80% and a pore size in the range of –2 microns.

Electrolyte 34 may be held in between the columns and within the pores of the electrolytic support layer. Hence, electrolytic support layer formed using the GLAD process is advantageous in that it permits the thickness of the overall electrolytic support layer to be that of a thin film, generally less than 5 micrometers thick or, preferably, less than 2 micrometers thick. Electrolyte 34 will not disperse and run off due to being held by plurality of columns 32. An electrolytic support layer may further include a thin coating 36 or film on first electrode, second electrode, third electrode, or a combination thereof. This is more particularly depicted in FIG. 2. Because the electrolytic support layer is desirably thin and electrode 22 is deposited on top of the electrolytic support layer, the time for gas to diffuse through it is shortened, thereby enabling electrochemical gas sensor 10 to have a quicker response time and a sensitivity to the sub ppb concentration range whereas conventional sensors generally have detection capabilities in the high ppb to ppm range.

Plurality of columns 32 includes known materials such as Silicon Dioxide, Magnesium Fluoride, or other porous insulating and insoluble mediums capable of absorbing electrolyte. The process for forming plurality of columns 32 includes a vapor deposition process and the material used to form plurality of columns may further include any material for supporting generation of vaporized material on substrate 12.

Figure 3:
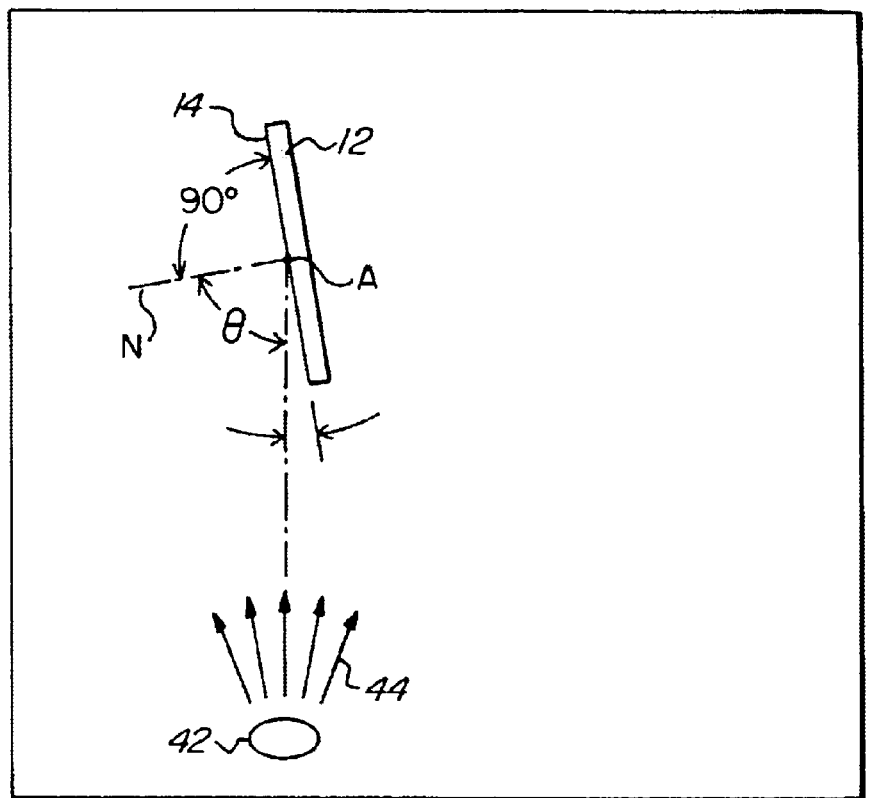
FIG. 3 depicts the process for forming a thin film of electrolyte support having a predetermined porosity for use as an electrolytic layer in the electrochemical gas sensor shown in FIG. 1.
Figure 4:
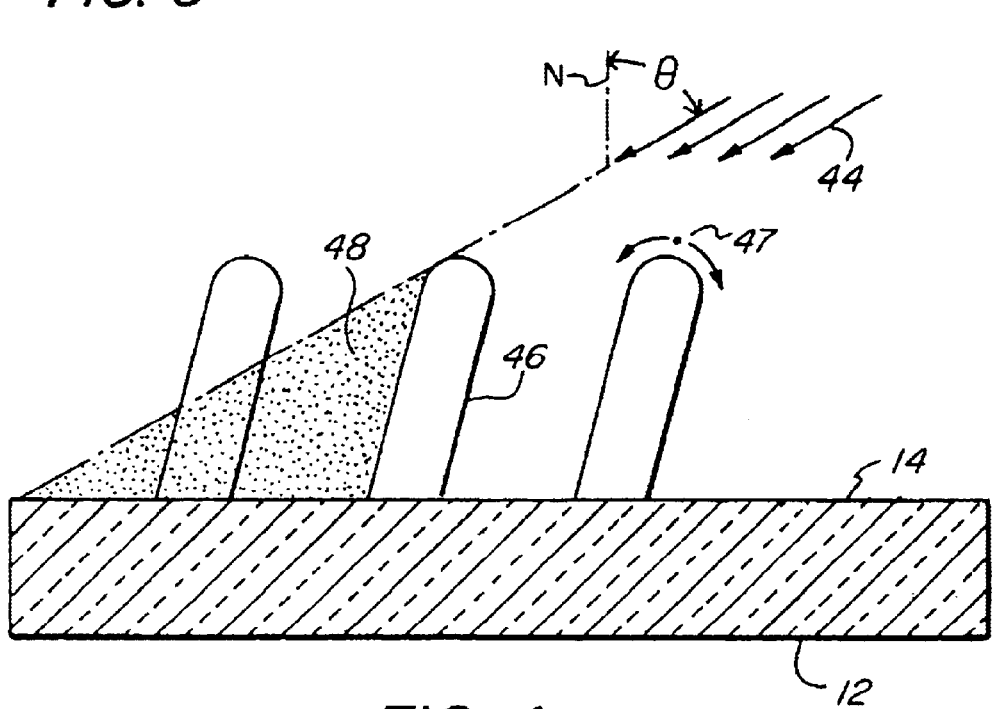
FIG. 4 depicts a plurality of columns formed during the process for forming a thin film of electrolyte support.
Figure 5A:
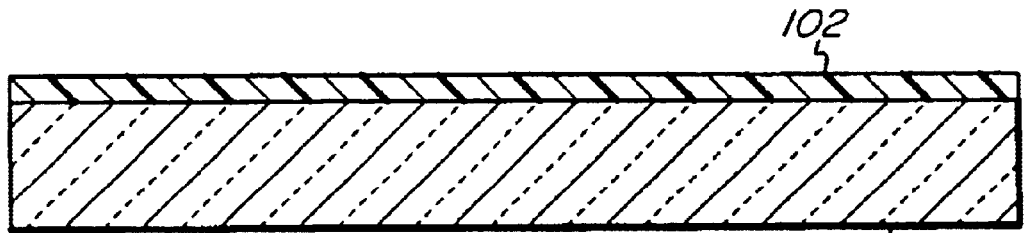
FIGS. 5 and 6 depict the stages of the process for providing the electrochemical gas sensor in accordance with the invention.
Figure 5B:
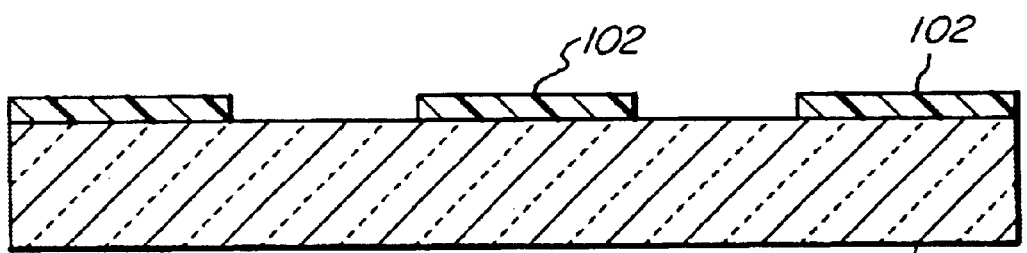
Figure 5C:
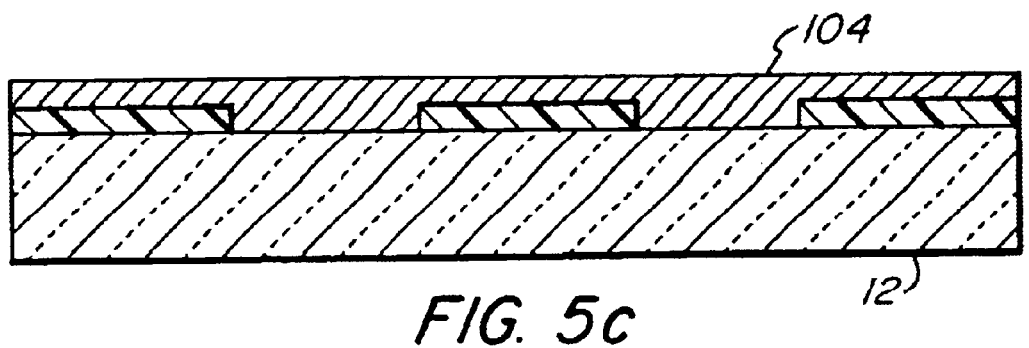
Figure 5D:
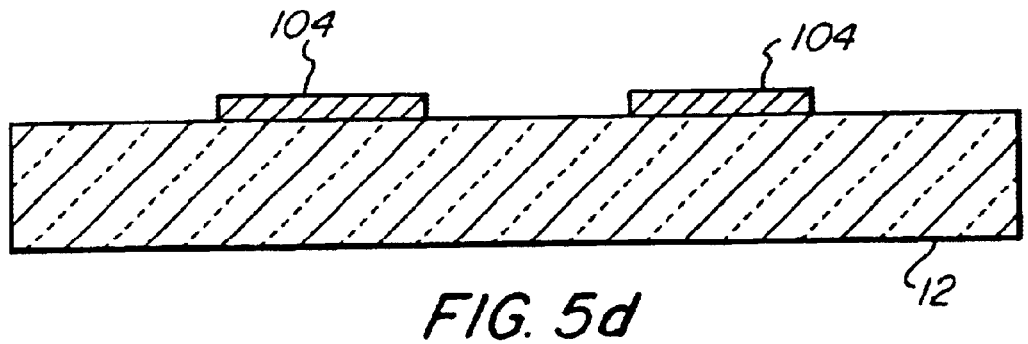
Figure 6A:
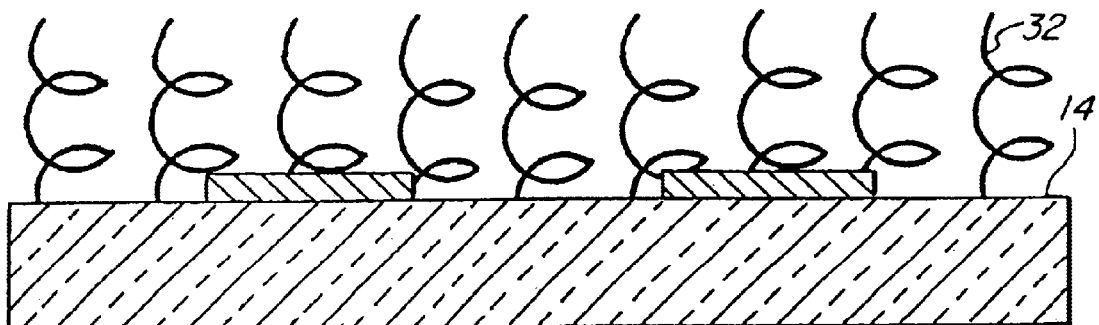
Figure 6B:
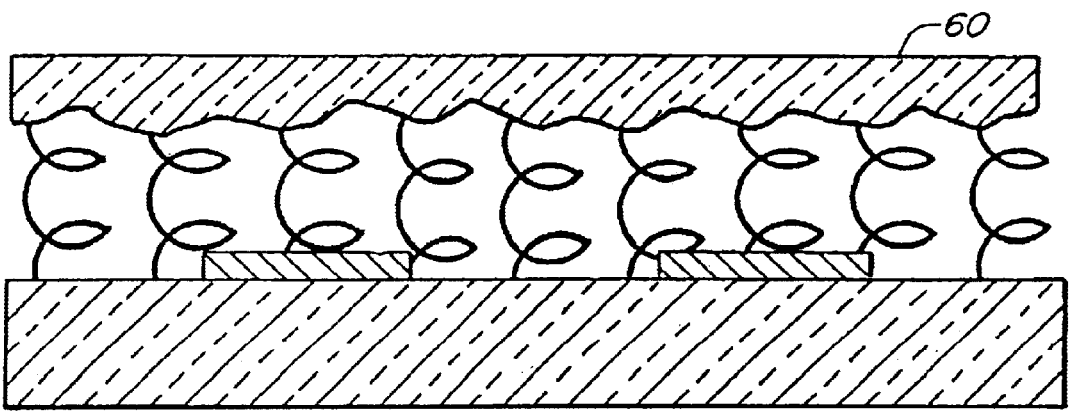
Figure 6C:
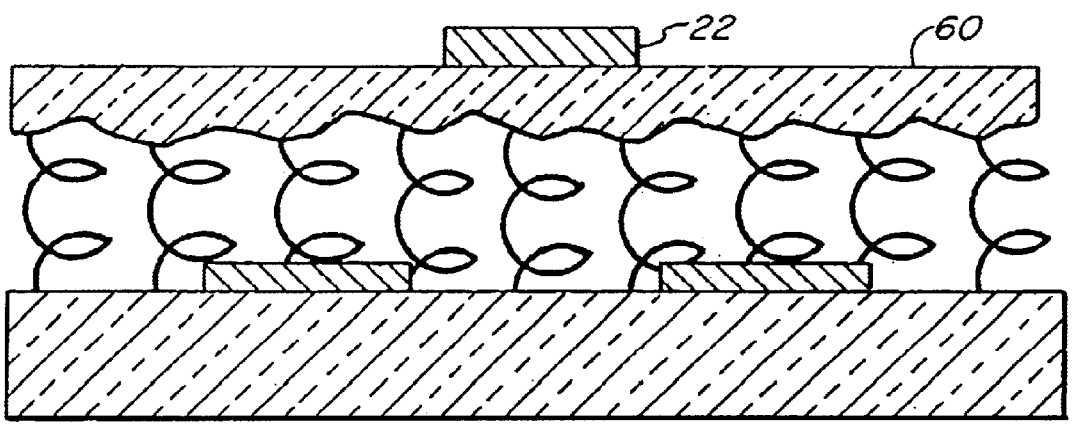

As depicted in FIG. 3, the process 36 for providing the thin film of electrolyte support begins with material, such as $SiO_2$, in a gaseous form 44 being directed from a known or novel source 42 towards surface 14 and electrodes that may already be deposited on surface 14. Sources may include a crucible of an electron beam evaporator or any source for emitting vapor. The formation, size, porosity, and definition of plurality of columns 32 are directly related to the angle of deposition θ of the vapor onto surface 14. The angles described herein are to be measured from the substrate normal, N, or plane perpendicular to surface 14. The reasoning behind the growth of columns from angular deposition lies in film growth in areas where atoms shadow adjacent regions 48, preventing disposition of vapor in these regions. As shown in FIG. 4, atoms in the vapor flux 44 continue to be deposited in regions that are not shadowed, thus forming columns 46. Atoms diffuse adatomically across the tops of the columns 47. Slanted columnar microstructures will grow if the angle θ is sufficiently large to create the shadowing effect, and there is limited adatom diffusion, such that adatom diffusion does not fill in the gaps between columns. In practice, θ need only be slightly above 0° to form defined columns. Columnar structures will form in many substances at θ=0°, though they may be hard to discern.

As vapor is being directed at substrate 12, substrate 12 is rotated about an axis parallel to surface 14 and rotation about such an axis alters angle θ. It should be known that an axis parallel to surface 14 is depicted as axis A for exemplary purposes only and that axis A can be any axis lying in a plane parallel to surface 14. Generally, the greater angle θ is, the more pronounced the columns are. As θ approaches 0°, or N, the columns begin to grow a cap 60. Capping is generally desirable for providing an area upon which second electrode 22 is deposited.

Two types of capping were investigated. In each case, θ generally was held at 85° for forming the plurality of columns. However, the degree of capping was varied. In the first instance, the helical films were capped to a minimum incidence angle of 60°, while in the second instance, capping continued to 0°, or N. Two sensors were produced and will be referred to as the 60° and 0° sensors, respectively. Sensing electrodes deposited over GLAD films of both the 60° and 0° sensors were tested and found to be electrically conductive over their entire length. Sensors capped to angles greater than 60°, however, were not found to be sufficiently continuous to allow functioning electrodes to be physically deposited thereon.

In another embodiment, it may be desirable for plurality of columns 32 to have a particular growth pattern under cap 60. This is desirable where porosity and/or pore size is to be increased. Growth patterns are formed by rotating substrate 12 about an axis normal to surface 14, or parallel to N. For exemplary purposes, N will represent the axis about which substrate 12 shall be rotated for forming a particular growth pattern under cap 60. Further, such rotation about axis N is independent of the rotation about axis A, meaning substrate 12 may be rotated about axis N whether or not θ equals zero.

Growth patterns include, but are not limited to, helices, zig zags, and posts or vertical columns. At angles where θ>80°, it was shown that the columns separate from one another entirely, introducing large pores into the film, or electrolytic support layer. As θ is increased, the pores grow larger and the overall electrolytic support layer density is reduced. This is desirable because the greater the porosity, the more electrolyte 34 is capable of being contained by the thin film of electrolyte support. This effect is the result of shadowing between neighboring columns 32. Helical microstructures are formed by a constant rotation back and forth about axis N. Zig zags are formed by a quick rotation between and a pause at a pair of angles that vary by 180°. Posts are produced by increasing the speed of rotation about axis N such that atomic diffusion eliminates the helical structure.

By similar methods, a number of additional specialized microstructures such as s-shapes and posts with periodic shifts in column angle, have also been produced. The helical structure is of particular interest. After first growing helices on substrate 12, θ is, thereafter, slowly reduced. As this happens, the shadowing conditions which originally led to porous thin films become less prominent. The helical columns begin to broaden and the overall film density begins to rise. Ultimately, the individual columns 32 broaden until they touch one another, resulting in the formation of a solid cap. If only partial densification of the film is required, the deposition may be stopped earlier.

Figure 2:
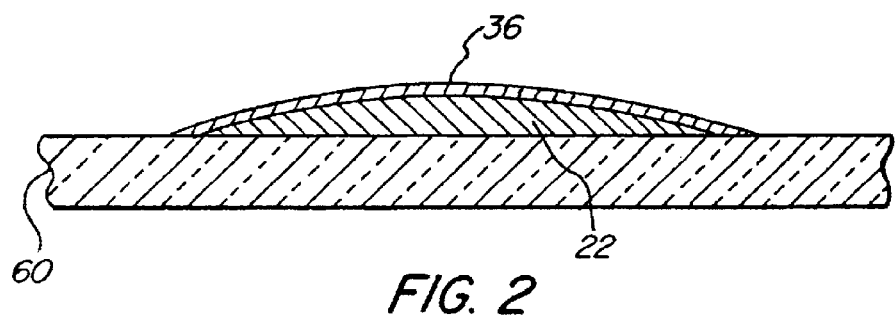
FIG. 2 more particularly depicts the sensing electrode as shown in FIG. 1.

FIG. 2 depicts a more detailed view of an electrode having coating 36 for preventing the electrode from being flooded with conductive medium or electrolyte 34. Coating 36 includes a thin film of electrolytic material that may be, but need not be, the same material as the electrolytic support layer. Coating 36 may be any material for preventing the electrode from being flooded including a hydrophobic film, such as Teflon. Flooding is an undesirable effect that reduces sensitivity and response time of sensor 10.

FIG. 5 depicts steps of process 100 for producing electrochemical gas sensor 10. As shown in FIG. 5, photoresist material 102 is spun onto substrate 12 (FIG. 5a). Using standard photolithograpy techniques, inverse images of the desired electrodes were subsequently patterned into the photoresist (FIG. 5b). The entire substrate was next sputter coated with the desired electrode material 104 (FIG. 5c). For exemplary purposes, 2000Å of platinum may be used. Subsequent immersion of the entire substrate in a bath of acetone results in the removal of all the platinum situated above areas coated with photoresist as well as the photoresist material itself (FIG. 5d).

FIG. 5e depicts the deposition of the electrolytic support layer using the GLAD process. The GLAD process includes all of the limitations specified above under plurality of columns 32, cap 60, and other discussions pertaining to the electrolytic support layer.

The plurality of columns formed and depicted in FIG. 5e is helically shaped. After forming the desired microstructure of the plurality of columns on surface 14 and the electrodes deposited on surface 14, the electrolytic layer is capped (FIG. 5f). Second electrode 22 is then deposited onto cap 60 by, desirably, a sputter coating method. Second electrode 22 is further desirably and optionally placed generally equidistant from first electrode 20 and third electrode 24 (FIG. 5g). The method for placing second electrode 22 may include masking.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An electrochemical gas sensor, comprising:
   a substrate having a surface;
   a first electrode deposited on said surface;
   a second electrode spaced apart from said surface;
   an electrolyte support placed between said surface and said second electrode and having a predetermined porosity, wherein said electrolyte support is in a solid state and comprises a plurality of columns; and where electrolyte is placed between said plurality of columns.

2. The electrochemical gas sensor according to claim 1, further including a coating on said second electrode for preventing flooding by said electrolyte.

3. The electrochemical gas sensor according to claim 1, wherein said electrolyte support further includes a cap.

4. The electrochemical gas sensor according to claim 1, wherein said plurality of columns are helix shaped.

5. The electrochemical gas sensor according to claim 1, wherein said electrolyte is an acid solution.

6. The electrochemical gas sensor according to claim 1, wherein said predetermined porosity is in the range of between 5% and 80%.

7. The electrochemical gas sensor according to claim 1, wherein said predetermined porosity is in the range of between 5% and 50%.

8. The electrochemical gas sensor according to claim 1, wherein said predetermined porosity includes a pore size in the range of between 0.0002 and 10 microns.

9. The electrochemical gas sensor according to claim 1, wherein said predetermined porosity includes a pore size in the range of between 0.0002 and 2 microns.

10. The electrochemical gas sensor according to claim 1, wherein said second electrode has a porosity magnitudes less than said electrolyte support.

11. The electrochemical gas sensor according to claim 1, wherein said second electrode further includes a porosity of less than 5% a and a pore size not exceeding the smaller of either a width or length of said second electrode at a pore's greatest measurement.

12. The electrochemical gas sensor according to claim 1, wherein said second electrode provides improved lamination to said electrolyte support.

* * * * *